United States Patent
Wu et al.

(10) Patent No.: US 10,545,710 B2
(45) Date of Patent: Jan. 28, 2020

(54) FLEXIBLE DEVICE

(71) Applicant: SHENZHEN ROYOLE TECHNOLOGIES CO., LTD., Guangdong (CN)

(72) Inventors: Weifeng Wu, Guangdong (CN); Xinyuan Xia, Guangdong (CN)

(73) Assignee: SHENZHEN ROYOLE TECHNOLOGIES CO., LTD., Shenzhen, Guangdong (CN)

(*) Notice: Subject to any disclaimer, the term of this patent is extended or adjusted under 35 U.S.C. 154(b) by 0 days.

(21) Appl. No.: 16/077,467

(22) PCT Filed: Jul. 19, 2016

(86) PCT No.: PCT/CN2016/090477
§ 371 (c)(1),
(2) Date: Aug. 11, 2018

(87) PCT Pub. No.: WO2018/014194
PCT Pub. Date: Jan. 25, 2018

(65) Prior Publication Data
US 2019/0034143 A1 Jan. 31, 2019

(51) Int. Cl.
*G06F 3/14* (2006.01)
*A61B 5/00* (2006.01)
*A44C 5/02* (2006.01)

(52) U.S. Cl.
CPC ........... *G06F 3/14* (2013.01); *A61B 5/681* (2013.01); *A44C 5/02* (2013.01)

(58) Field of Classification Search
CPC ............ G06F 3/14; A44C 5/107; A61B 5/681

USPC ........................................... 340/573.1
See application file for complete search history.

(56) References Cited

U.S. PATENT DOCUMENTS

| | | | | |
|---|---|---|---|---|
| 2014/0078046 A1* | 3/2014 | Seo | ....... | G06F 1/1652 345/156 |
| 2015/0089974 A1 | 4/2015 | Seo | | |
| 2016/0292365 A1* | 10/2016 | Chi | ....... | A61B 5/681 |
| 2016/0306393 A1* | 10/2016 | Huitema | ....... | G06F 3/0346 |
| 2016/0371043 A1* | 12/2016 | Gupta | ....... | G06F 3/14 |
| 2017/0017313 A1* | 1/2017 | Rakshit | ....... | G06F 3/0488 |
| 2017/0061932 A1* | 3/2017 | Kwon | ....... | G06F 3/0412 |
| 2017/0090558 A1* | 3/2017 | Gao | ....... | G06F 3/013 |
| 2017/0091340 A1* | 3/2017 | Yoon | ....... | G06F 1/1652 |
| 2017/0308346 A1* | 10/2017 | Lee | ....... | G06F 3/14 |
| 2019/0034143 A1* | 1/2019 | Wu | ....... | G06F 3/14 |

FOREIGN PATENT DOCUMENTS

| | | | |
|---|---|---|---|
| CN | 104614975 A | 5/2015 | |
| CN | 105700841 A | 6/2016 | |

OTHER PUBLICATIONS

Office Action for China Application No. 201680025664.0 dated Nov. 23, 2018 (with English translation).
International Search Report for PCT/CN2016/090477 dated May 2, 2017.

* cited by examiner

*Primary Examiner* — Omar Casillashernandez
(74) *Attorney, Agent, or Firm* — IPro, PLLC; Na Xu

(57) ABSTRACT

A flexible device includes: a functional element: a first movable element; a second movable element movably connected with the first movable element, in which a movement of the second movable element relative to the first moveable element drives the flexible device to deform.

19 Claims, 14 Drawing Sheets

FLEXIBLE DEVICE

This application is a national phase application of International Application No. PCT/CN2016/090477, filed Jul. 19, 2016, the entire contents of which are incorporated herein by reference.

FIELD

The present disclosure relates to a flexible device, and more particularly to a flexible wearable device.

BACKGROUND

More and more wearable smart devices, such as smart watches, smart bracelets, smart shoes, smart clothes, intelligent knapsacks, etc., are designed as more attention is paid to health. Various sensors are integrated in the smart devices to monitor the data of human body, so as to maintain health.

Smart bracelet, due to its small size and light weight, has become one of the most popular wearable smart devices. However, the existing smart bracelet has basically fixed shape and cannot meet the application requirements at different occasions.

SUMMARY

Embodiments of the present disclosure provide a flexible device, which meets the application requirements at different occasions.

In embodiments of the present disclosure, there is provided a flexible device, including a functional element; a first movable element; a second movable element movably connected with the first movable element, in which a movement of the second movable element relative to the first moveable element drives the flexible device to deform.

In embodiments of the present disclosure, the movement of the second movable element relative to the first movable element comprises translation and rotation.

In embodiments of the present disclosure, the movement of the second movable element relative to the first movable element is switched between a first state and a second state, in which in the first state, the second movable element extends relative to the first movable element, and in the second state, the second movable element retracts relative to the first movable element.

In embodiments of the present disclosure, the second movable element defines a rotation center, and the rotation of the second movable element around the rotation center drives the flexible device to deform.

In embodiments of the present disclosure, the rotation center of the second movable element is higher than a top part of the second movable element.

In embodiments of the present disclosure, hardness of a lower part of the functional element is greater than that of an upper part of the functional element, and the rotation center of the second movable element is higher than the lower part of the functional element.

In embodiments of the present disclosure, top surfaces of the first movable element and the second movable element each include a convex surface.

In embodiments of the present disclosure, the convex surfaces of the first movable element and the second movable element are each an arc surface.

In embodiments of the present disclosure, in the second state, the convex surfaces of the first movable element and the second movable element together constitute a continuous arc surface.

In embodiments of the present disclosure, in the second state, projections of the convex surfaces of the first movable element and the second movable element in a plane perpendicular to the convex surfaces together form a continuous arc.

In embodiments of the present disclosure, in the first state, the convex surfaces of the first movable element and the second movable element are not distributed continuously.

In embodiments of the present disclosure, the functional element includes a supporting plate and a flexible functional screen attached to the supporting plate; the supporting plate includes a first surface fixed to the flexible functional screen, and a second surface fixed to the first movable element and the second movable element; and the first surface and the second surface are disposed on two opposite sides of the supporting plate, respectively.

In embodiments of the present disclosure, the rotation center of the second movable element is higher than the first surface of the supporting plate.

In embodiments of the present disclosure, the second surface of the supporting plate is fixed to top parts of the top surfaces of the first movable element and the second movable element; in the first state, the second surface of the supporting plate separates from other parts of the top surfaces of the first movable element and the second movable element; and in the second state, the second surface of the supporting plate contacts with other parts of the top surfaces of the first movable element and the second movable element.

In embodiments of the present disclosure, a contact area between the supporting plate and the top surface of the second movable element in the second state is greater than that in the first state.

In embodiments of the present disclosure, a hardness of the supporting plate is greater than that of the flexible functional screen.

In embodiments of the present disclosure, a ratio of a distance between the rotation center of the second movable element and the first surface of the supporting plate to a thickness of the supporting plate is between 0.1 and 0.5.

In embodiments of the present disclosure, a location of the rotation center of the second movable element relative to the first movable element is constant when the second movable element moves relative to the first movable element.

In embodiments of the present disclosure, the second movable element is staggeredly connected with the first movable element.

In embodiments of the present disclosure, a rotation trajectory of the second movable element around the rotation center is in an arc shape, and a bending direction of the arc trajectory of the second movable element is opposite to that of the top surface of the second movable element.

In embodiments of the present disclosure, the second movable element provides an arc positioning slot, along which the second movable element is configured to move relative to the first movable element, two opposite ends of the positioning slot are near the top surface of the second movable element, and a middle part of the positioning slot is away from the top surface of the second movable element.

In embodiments of the present disclosure, a bending direction of the positioning slot is opposite to that of the top surface of the second movable element.

BRIEF DESCRIPTION OF THE DRAWINGS

Drawings which will be involved in the following description of embodiments will be introduced below in brief for illustrating technical solutions in embodiments of the present disclosure more clearly, it will be appreciated that drawings described below are just some implementations of the present disclosure, and other modifications can also be obtained by those who skilled in the art, without creative work.

DETAILED DESCRIPTION

In the following, embodiments of the present disclosure will be described clearly with reference to drawings.

Figure 1:
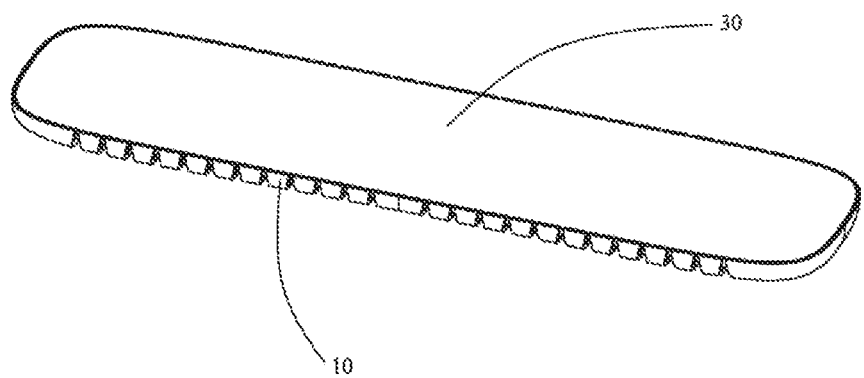
FIG. 1 is a schematic view of a flexible device according to embodiments of the present disclosure.
Figure 2:
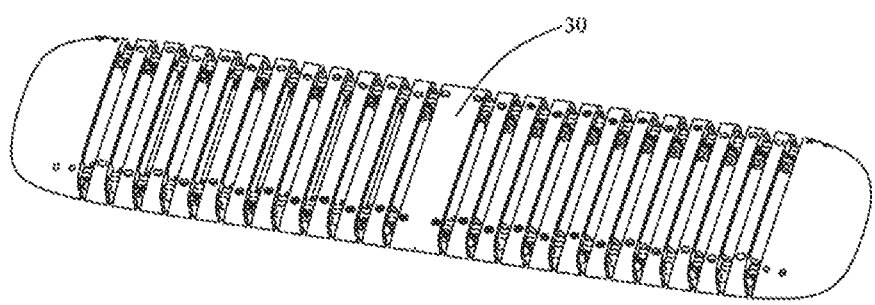
FIG. 2 is an inverted view of the flexible device as shown in FIG. 1.
Figure 3:
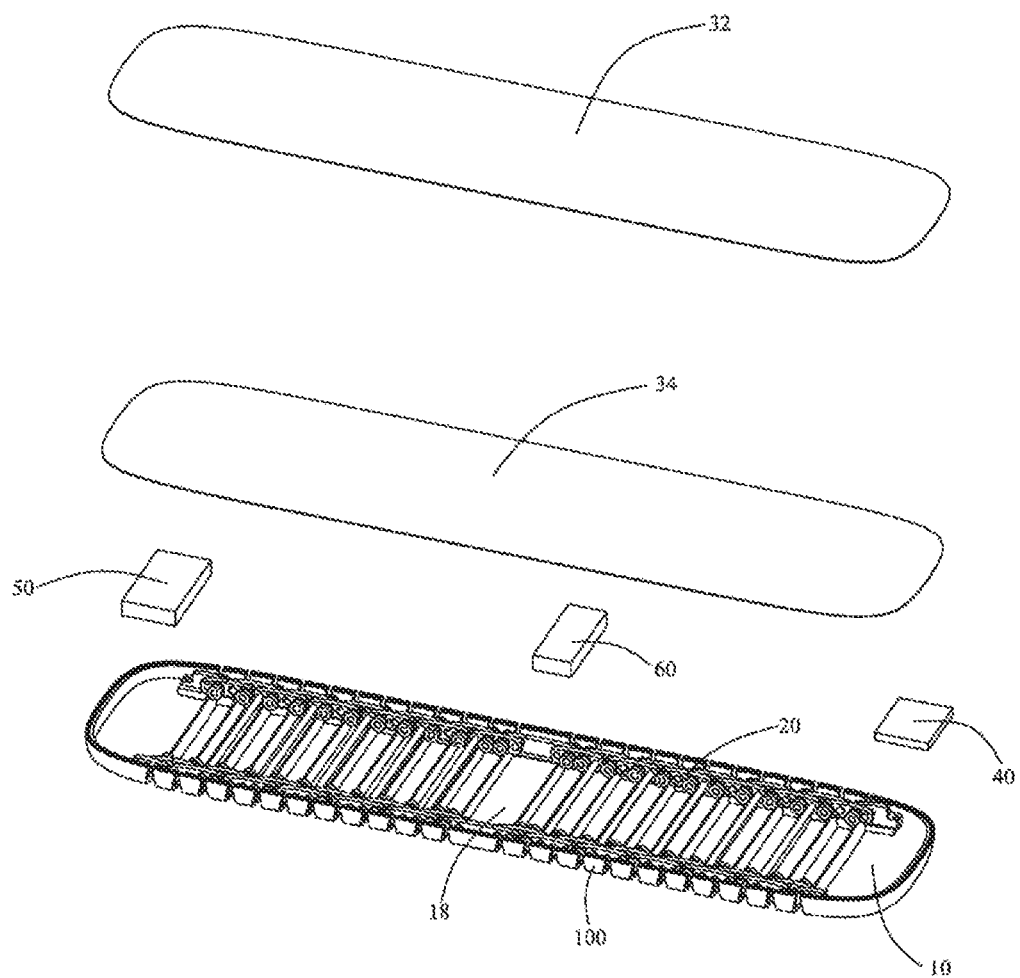
FIG. 3 is a partial explosive view of the flexible device as shown in FIG. 1.

Referring to FIGS. 1-3, which illustrate a flexible device according to embodiments of the present disclosure, the flexible device includes a casing 10, a flexible assembly 20 disposed in the casing 10 and a functional element 30 disposed on the casing 10. The flexible assembly 20 is deformable so as to drive the flexible device to deform, thereby enabling the flexible device to adapt to the application requirements at different occasions.

Figure 4:
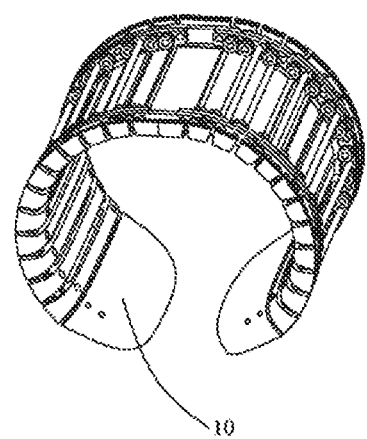
FIG. 4 is a schematic view of the flexible device as shown in FIG. 1 which is deformed into a bracelet, where functional elements are removed.

Further referring to FIG. 4, the deformation of the flexible device includes a transformation from a plate shape to a ring shape. When the flexible device is in the plate shape, the flexible device is spread out to facilitate users to operate; when the flexible device is in the ring shape, the flexible device is curled to facilitate users to wear as a wearable device. Of course, the deformation of the flexible device may include other types, which can be determined according to requirements, so as to meet the needs of more application occasions. For example, the flexible device may be transformed from an arch shape to a ring shape, from a plate shape to a wave-shape, or from a U shape to an S shape.

Figure 5:
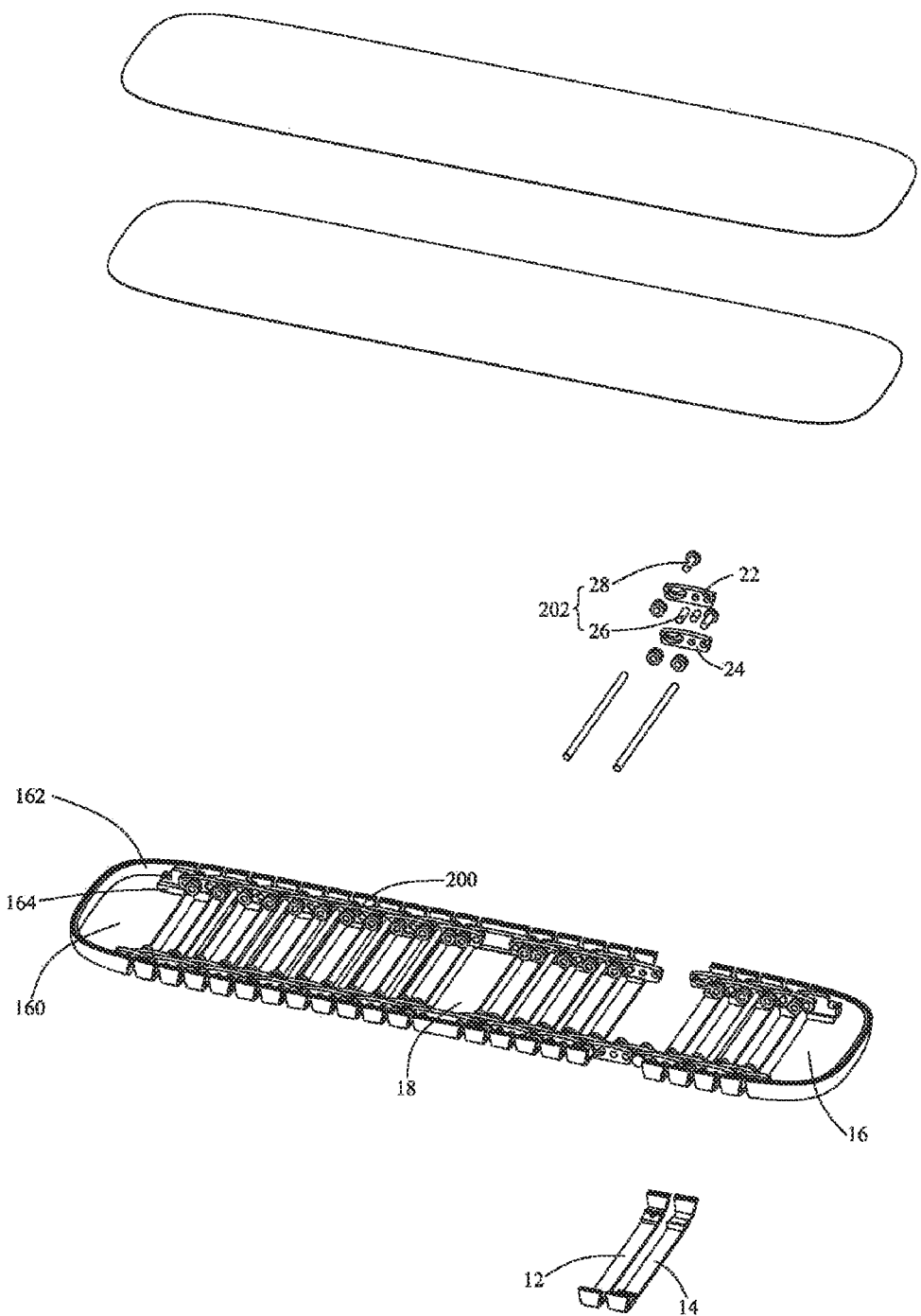
FIG. 5 is a further explosive view of the flexible device as shown in FIG. 3.
Figure 6:
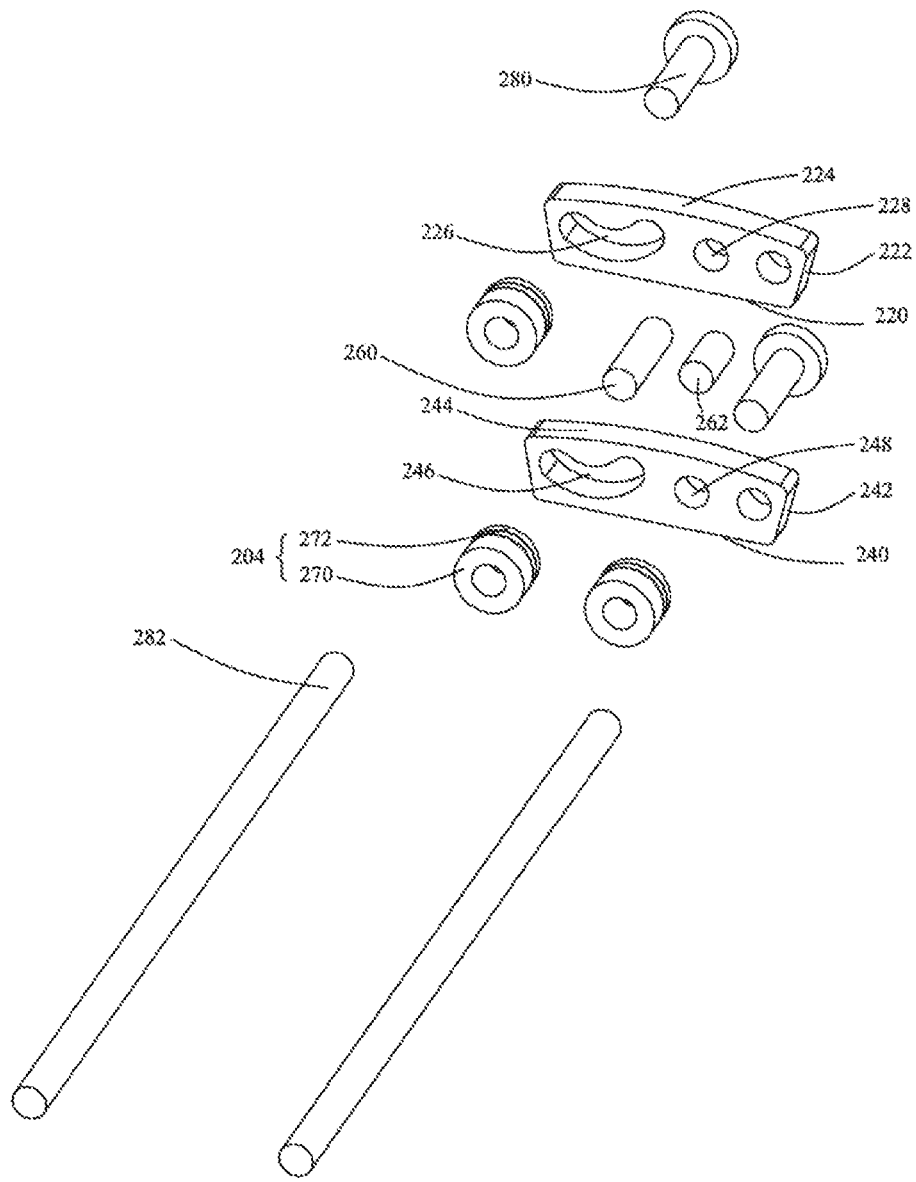
FIG. 6 is a partial enlarged view of the flexible device as shown in FIG. 5.
Figure 7:
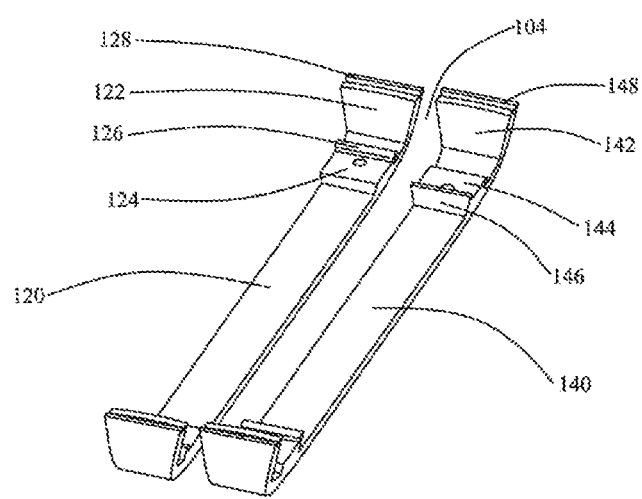
FIG. 7 is another partial enlarged view of the flexible device as shown in FIG. 5.

Further referring to FIGS. 5-7, the flexible assembly 20 includes movable elements 200 positioned at each of two opposite sides of the casing 10. The movable element 200 positioned at each side of the casing 10 includes a first movable element 22 and a second movable element 24 movably connected with the first movable element 22. In embodiments of the present disclosure, there are a plurality of the first movable elements 22 and a plurality of the second movable elements 24, and both of the plurality of the first movable elements 22 and the plurality of the second movable elements 24 are distributed at each of the two opposite sides of the casing 10. That is, at each side of the casing 10, there are provided with several first movable elements 22 and several second movable elements 24. The first movable elements 22 are closer to an outer side of the casing 10 than the second movable elements 24. The first movable elements 22 at each side of the casing 10 are linearly aligned, each of the first movable elements 22 is not directly connected with an adjacent one. The second movable elements 24 at each side of the casing 10 are linearly aligned, each of the second movable elements 24 is not directly connected with an adjacent one. The first movable elements 22 and the second movable elements 24 adjacent thereto disposing at the same side of the casing 10 are staggeredly connected with each other. Particularly, each first movable element 22 is parallel to two second movable elements 24 adjacent thereto and each first movable element 22 is staggeredly connected with the two second movable elements 24.

The first movable element 22 and the second movable element 24 have the same shape and structure. In an embodiment of the present disclosure, both the first movable element 22 and the second movable element 24 are hinges. The first movable element 22 is substantially trapezoidal in shape, and includes a flat bottom surface 220, two inclined side surfaces 222 and a bended top surface 224. The bottom surface 220 of the first movable element 22 is a plane, and is parallel to the functional element 30 when the functional element 30 is not deformed. Each side surface 222 of the first movable element 22 is a plane and is inclined relative to the bottom surface 220. An inner angle between each side surface 222 and the bottom surface 220 is an obtuse angle, which is greater than 90 degrees and less than 180 degrees. To be optimized, the angle is greater than 100 degrees and less than 110 degrees. The two side surfaces 222 extend upward in opposite directions to connect the bottom surface 220 and the top surface 224. The top surface 224 of the first movable element 22 is an arch surface, which forms a supporting surface of the first movable element 22. Height of the top surface 224 gradually increases from two opposite ends to a middle part thereof, and a convex surface is formed thereby. It will be appreciated that, the top surface 224 may also be other types of convex surfaces, such as a convex surface having a shape of half of a hexahedron (similar to trapezoid), a convex surface having a shape of half of an octahedron (similar to a trapezoid plus a rectangle below the trapezoid), a convex surface having a shape of half of a decahedron and so on. Herein, an angle formed by two opposite end points of an arc surface with a center of a circle where the arc surface is located is defined as a span angle. A span angle of the top surface 224 is greater than 10 degrees and less than 30 degrees.

The first movable element 22 is provided with a positioning slot 226. The positioning slot 226 is communicated with a front surface (i.e., an inner surface of the first movable element 22) and a rear surface (i.e., an outer surface of the first movable element 22) of the first movable element 22, and is close to one of the two side surfaces 222 of the first movable element 22. The positioning slot 226 is in an arc shape, and its bending direction is opposite to that of the top surface 224. Height of the positioning slot 226 gradually decreases from two opposite ends to a middle part thereof. The positioning slot 226 includes a first arc surface, a second arc surface and two arc connecting surfaces connecting the first arc surface and the second arc surface. The first arc surface is parallel to and concentric with the second arc surface. A length of the first arc surface is less than that of the second arc surface. The arc connecting surface is substantially semicircular in shape, so as to form fillets at the two opposite ends of the positioning slot 226. A span angle of the positioning slot 226 is greater than that of the top surface 224. In an embodiment of the present disclosure, the span angle of the positioning slot 226 is greater than 70 degrees and less than 90 degrees.

The first movable element 22 is further provided with a positioning hole 228. The positioning hole 228 is also communicated with the front surface and the rear surface of the first movable element 22. In embodiments of the present disclosure, the positioning hole 228 includes a first positioning hole and a second positioning hole. The first positioning hole is close to a middle part of the first movable element 22, and the second positioning hole is close to the other of the two side surfaces 222 of the first movable element 22. The positioning hole 228 is higher than a lowest point of the positioning slot 226 and is lower than a highest point of the positioning slot 226.

As the second movable element 24 has a same shape and structure with the first movable element 22, parts included in the second movable element 24 and sizes and positions of the parts can be referred to that of the first movable element 22. The second movable element 24 is substantially trapezoidal in shape, and includes a flat bottom surface 240, two inclined side surfaces 242, and a bended top surface 244. The bottom surface 240 of the second movable element 24 is a plane, and is parallel to the functional element 30 when the functional element 30 is not deformed. Each side surface 242 is a plane and is inclined relative to the bottom surface 240. An inner angle between each side surface 242 and the bottom surface 240 is an obtuse angle, which is greater than 90 degrees and less than 180 degrees, such as greater than 100 degrees and less than 110 degrees. The two side surfaces 242 extend upward in opposite directions to connect the bottom surface 240 and the top surface 244. The top surface 244 of the second movable element 24 is an arch surface, which forms a supporting surface of the second movable element 24. Height of the top surface 244 gradually increases from two opposite ends to a middle part thereof, and a convex surface is formed thereby. A span angle of the top surface 244 is greater than 10 degrees and less than 30 degrees. It will be appreciated that, the top surface 224 may also be other types of convex surfaces, such as a convex surface having a shape of half of a hexahedron, a convex surface having a shape of half of an octahedron, a convex surface having a shape of half of a decahedron and so on.

The second movable element 24 is provided with a positioning slot 246. The positioning slot 246 is communicated with a front surface (i.e., an inner surface) and a rear surface (i.e., an outer surface) of the second movable element 24, and is close to one of the two side surfaces 242 of the second movable element 24. The positioning slot 246 is in an arc shape, and its bending direction is opposite to that of the top surface 244. Height of the positioning slot 246 gradually decreases from two opposite ends to a middle part thereof. The positioning slot 246 includes a first arc surface, a second arc surface and two arc connecting surfaces for connecting the first arc surface and the second arc surface. The first arc surface is parallel to and concentric with the second arc surface. A length of the first arc surface is less than that of the second arc surface. The arc connecting surface is substantially semicircular in shape, so as to form fillets at the two opposite ends of the positioning slot 246. A span angle of the positioning slot 246 is greater than that of the top surface 244. In an embodiment of the present disclosure, the span angle of the positioning slot 246 is greater than 70 degrees and less than 90 degrees.

The second movable element 24 is further provided with a positioning hole 248. The positioning hole 248 is also communicated with the front surface and the rear surface of the second movable element 24. In embodiments of the present disclosure, the positioning hole 248 includes a first positioning hole and a second positioning hole. The first positioning hole is close to a middle part of the second movable element 24, and the second positioning hole is close to the other of the two side surfaces 242 of the second movable element 24. The positioning hole 248 is higher than a lowest point of the positioning slot 246 and is lower than a highest point of the positioning slot 246.

The flexible assembly 20 further includes a positioning element 202 connected with the movable element 200. Particularly, the first movable element 22 is staggeredly connected with the second movable element 24 adjacent thereto through the positioning element 202, and part of the front surface of the first movable element 22 is in contact with part of the rear surface of the second movable element 24. The positioning element 202 can slide in the positioning slots 226, 246, thereby driving the first movable element 22 to move relative to the second movable element 24. In embodiments of the present disclosure, the positioning element 202 includes a first positioning element 26 and a second positioning element 28. The second positioning element 28 is configured to connect the first movable element 22 with one of the two second movable elements 24 adjacent to the first movable element 22, and the first positioning element 26 is configured to connect the first movable element 22 with the other of the two second movable elements 24 adjacent to the first movable element 22. Structure of the second positioning element 28 may be same with or different from that of the first positioning element 26. In embodiments of the present disclosure, the first positioning element 26 include a first positioning shaft 260 and a second positioning shaft 262, and the second positioning element 28 include a first positioning shaft 280 and a second positioning shaft 282. The first positioning shaft 280 and the second positioning shaft 282 of the second positioning element 28 pass through the positioning slot 226 of the first movable element 22 and then respectively pass through two positioning holes 248 of one of the two second movable elements 24 adjacent to the first movable element 22; and the first positioning shaft 260 and the second positioning shaft 262 of the first positioning element 26 respectively pass through the two positioning holes 228 of the first movable element 22 and then pass through the positioning slot 246 of the other of the two second movable elements 24 adjacent to the first movable element 22. The first positioning shaft 260 and the second positioning shaft 262 of the first positioning element 26 are spaced apart from each other, and a distance between the first positioning shaft 260 and the second positioning shaft 262 is unchanged with the deformation of the flexible assembly 20. The first positioning shaft 280 and the second positioning shaft 282 of the second positioning element 28 are spaced apart from each other, and a distance between the first positioning shaft 280 and the second positioning shaft 282 is unchanged with the deformation of the flexible assembly 20.

The first positioning shaft 280 and the second positioning shaft 282 of the second positioning element 28 may have the same or different structures; and the first positioning shaft 260 and the second positioning shaft 262 of the first positioning element 26 may have the same or different structures. The structure of the first positioning shaft 280 of the second positioning element 28 may be the same with or different from that of the first positioning shaft 260 or the second positioning shaft 262 of the first positioning element 26; and the structure of the second positioning shaft 282 of the second positioning element 28 may be the same with or different from that of the first positioning shaft 260 or the second positioning shaft 262 of the first positioning element 26. In embodiments of the present disclosure, the structures of the first positioning shaft 280 and the second positioning shaft 282 of the second positioning element 28 and the first positioning shaft 260 and the second positioning shaft 262 of the first positioning element 26 are different from one another. The second positioning shaft 282, the first positioning shaft 280, the first positioning shaft 260 and the second positioning shaft 262 decrease successively in length. The first positioning shaft 280 of the second positioning element 28 includes a screw, and the screw includes a nut and a threaded rod vertically extending from the nut. The threaded rod passes through a positioning slot 226 of a first movable element 22 and enters into one of two positioning holes 248 of one of two second movable elements 24 adjacent to the first movable element 22. The nut is abutted against the rear surface of the first movable element 22 to prevent the first positioning shaft 280 from falling off. The second positioning shaft 282 of the second positioning element 28 includes a continuous connecting rod, which has a longitudinal structure. The connecting rod passes though the positioning slot 226 of the first movable element 22 and the other of the two positioning holes 248 of the one of the two second movable elements 24 adjacent to the first movable element 22 at one of the two opposite sides of the flexible device, and passes through a positioning hole 248 of a second movable element 24 at the other of the two opposite sides of the flexible device and a positioning slot 226 of a first movable element 22 adjacent to the second movable element 24 at the other of the two opposite sides of the flexible device. Thereby, the connecting rod connects the movable elements 200 at the two opposite sides of the flexible device, in particular, connects the first movable element 22 and the second movable element 24 of the movable element 200 at one of the two opposite sides of the flexible device with the first movable element 22 and the second movable element 24 of the movable element 200 at the other of the two opposite sides of the flexible device, so as to strengthen the structure of the flexible device. The first positioning shaft 260 of the first positioning element 26 includes a threaded rod, which passes through one of two positioning holes 228 of the first movable element 22 and enters into the positioning slot 246 of the other of the two second movable elements 24 adjacent to the first movable element 22. The second positioning shaft 262 of the first positioning element 26 includes a pillar, which passes through the other of the two positioning holes 228 of the first movable element 22 and enters into the positioning slot 246 of the other of the two second movable elements 24 adjacent to the first movable element 22. The first positioning shaft 280 of the second positioning element 28 connects the first movable element 22 with one of the two second movable elements 24 adjacent to the first movable element 22 at the same side of the flexible device; the second positioning shaft 282 of the second positioning element 28 connects the first movable element 22 and one of the two second movable elements 24 adjacent to the first movable element 22 at one of the two opposite sides of the flexible device with the first movable element 22 and one of the two second movable elements 24 adjacent to the first movable element 22 at the other of the two opposite sides of the flexible device; the first positioning shaft 260 of the first positioning element 26 connects the first movable element 22 with the other of the two second movable elements 24 adjacent to the first movable element 22 at the same side of the flexible device; and the second positioning shaft 262 of the first positioning element 26 connects the first movable element 22 with the other of the two second movable elements 24 adjacent to the first movable element 22 at the same side of the flexible device. Diameters of the first positioning shaft 280 and the second positioning shaft 282 are equal to or slightly less than a width of the positioning slot 226, such that the first positioning shaft 280 and the second positioning shaft 282 can be closely fitted in the positioning slot 226; and diameters of the first positioning shaft 260 and the second positioning shaft 262 are equal to or slightly less than a width of the positioning slot 246, such that the first positioning shaft 260 and the second positioning shaft 262 can be closely fitted in the positioning slot 246. A distance between the first positioning shaft 280 and the second positioning shaft 282 of the second positioning element 28 is less than the length of the positioning slot 226, such that the first positioning shaft 280 and the second positioning shaft 282 can slide in the positioning slot 226; and a distance between the first positioning shaft 260 and the second positioning shaft 262 of the first positioning element 26 is less than the length of the positioning slot 246, such that the first positioning shaft 260 and the second positioning shaft 262 can slide in the positioning slot 246, thereby driving the first movable element 22 to move relative to the second movable element 24.

The flexible assembly 20 further includes a restricting element 204 abutted against the movable element 200 and the restricting element 204 is movably sleeved on the positioning element 202 such that a force is controlled to be applied to the movable element 200, thus adjusting a damping when the flexible assembly 20 is deformed. Particularly, the first positioning shaft 280 of the second positioning element 28 is locked in the restricting element 204 after passing through the positioning slot 226, and the first positioning shaft 260 of the first positioning element 26 is locked in the restricting element 204 after passing through the positioning slot 246. In embodiments of the present disclosure, the restricting element 204 is a nut 270 with an elastic piece 272, and is locked with the first positioning shaft 260 or the first positioning shaft 280 through threads. The elastic piece 272 is elastically abutted against and disposed between the nut 270 and the front surface of the first movable element 22 or the second movable element 24. Moreover, an elastic force supplied by the elastic piece 272 to the first movable element 22 or the second movable element 24 can be adjusted by adjusting a locking degree between the restricting element 204 and the first positioning shaft 260 or the first positioning shaft 280, so as to control the damping of the flexible assembly when the flexible assembly 20 rotates. The flexible assembly 20 can be kept in any state if the damping is adjusted to a suitable value, so as to meet different needs for shape.

When the functional element 30 includes a flexible functional screen 32, such as a flexible touch screen, a flexible display or a combination thereof, due to properties of the material itself, the flexible functional screen 32 is not resistant to stretch or compression. In order to reduce or even prevent the stretch or compression of the flexible functional screen 32 when the flexible device is deformed, the present disclosure further provides embodiments where the structures and connecting relationship of the first movable element 22 and the second movable element 24 are further improved.

Figure 11:
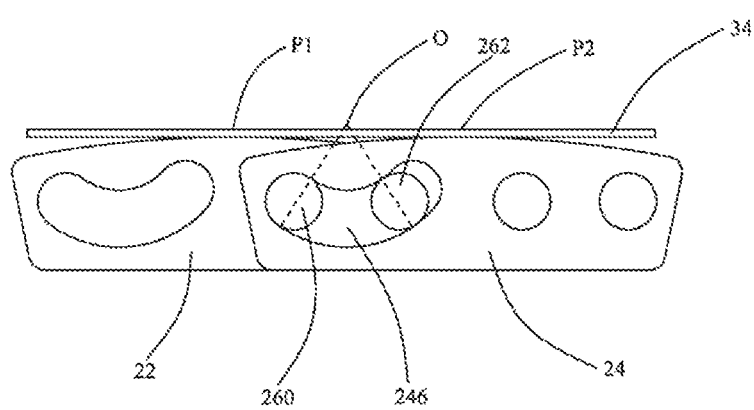
FIG. 11 is schematic diagram of a first movable element and a second movable element of the flexible device as shown in FIG. 1 in a first state.
Figure 12:
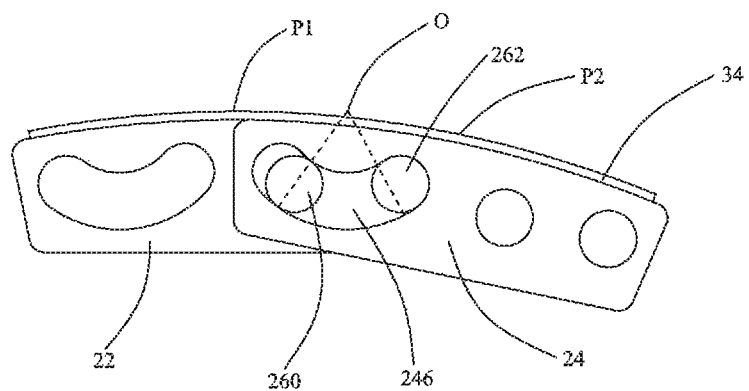
FIG. 12 is schematic diagram of a first movable element and a second movable element of the flexible device as shown in FIG. 1 in a second state.

Further referring to FIGS. 11-12, as the flexible touch screen or the flexible display includes a flexible material, in order to facilitate operations or watching, the functional element 30 further includes a supporting plate 34 fixed below the flexible touch screen or the flexible display. The supporting plate 34 has the same area and shape as that of the flexible functional screen 32, and is made of an elastic material with a higher hardness, such as a steel sheet, an iron sheet, a copper sheet and so on. Hardness of the supporting plate 34 is greater than that of the flexible functional screen 32. The supporting plate 34 is fixed on the first movable element 22 and the second movable element 24. In embodiments of the present disclosure, the supporting plate 34 is fixed on the supporting surfaces (i.e., top surfaces 224, 244) of the first movable element 22 and the second movable element 24. As the supporting surfaces are convex arc surfaces, the supporting plate 34 is fixed to top parts of the supporting surfaces, i.e., fixing points of the supporting surface are the top parts of the supporting surfaces. Certainly, if the top surfaces 224, 244 of the first movable element 22 and the second movable element 24 are in other shapes, the fixing points may also be other position points on the top surfaces 224, 244 of the first movable element 22 and the second movable element 24. Further, term "fixing point" is merely for convenience of description, which essentially refers to the top parts of the top surfaces 224, 244 and may include a region, and thus shall not be construed or limited to a certain single point. The supporting plate 34 is fixed to the top part of the top surface 224, 244 of each of the first movable elements 22 and the second movable elements 24 at each side of the flexible device, and is separated from other parts of the top surface 224, 244 of the first movable element 22 and the second movable element 24. The supporting plate 34 may be fixed to the first movable element 22 and the second movable element 24 by means of welding and bonding.

As the positioning slot 246 of the second movable element 24 is in the arc shape, when the second movable element 24 moves relative to the first movable element 22, the positioning slot 246 of the second movable element 24 is restricted by the first positioning shaft 260 and the second positioning shaft 262 of the first positioning element 26 connecting the first movable element 22 and the second movable element 24, such that the second movable element 24 moves along a trajectory of the positioning slot 246. Specifically, when the second movable element 24 rotates relative to the first movable element 22, the second movable element 24 also translates relative to the first movable element 22, that is, the movement of the second movable element 24 relative to the first movable element 22 includes both a rotation and a translation. A rotation direction of the second movable element 24 is clockwise relative to the first movable element 22, and a translation direction of the second movable element 24 is towards the positioning slot 226 of the first movable element 22.

Figure 13:
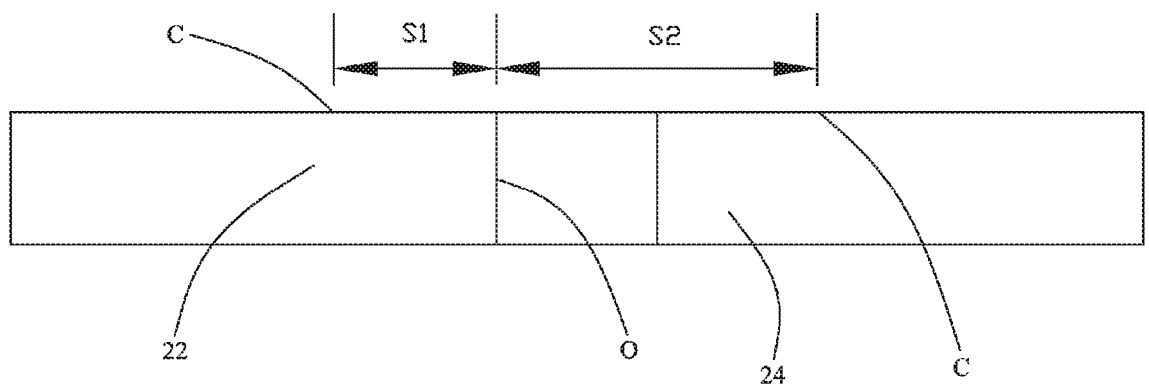
FIGS. 13-15 are schematic diagrams illustrating a state switching principle of the first movable element and the second movable element as shown in FIGS. 11-12.
Figure 14:
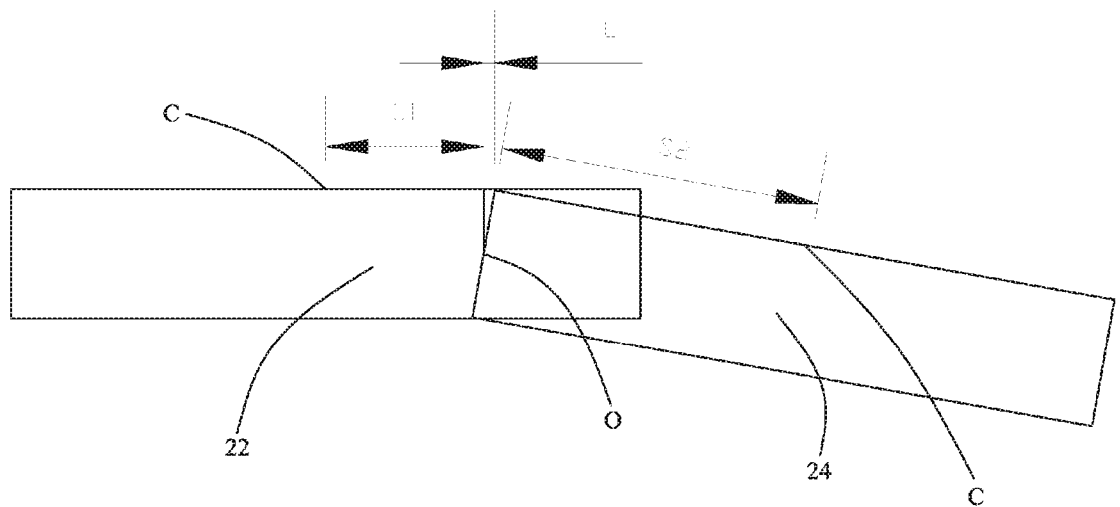
Figure 15:
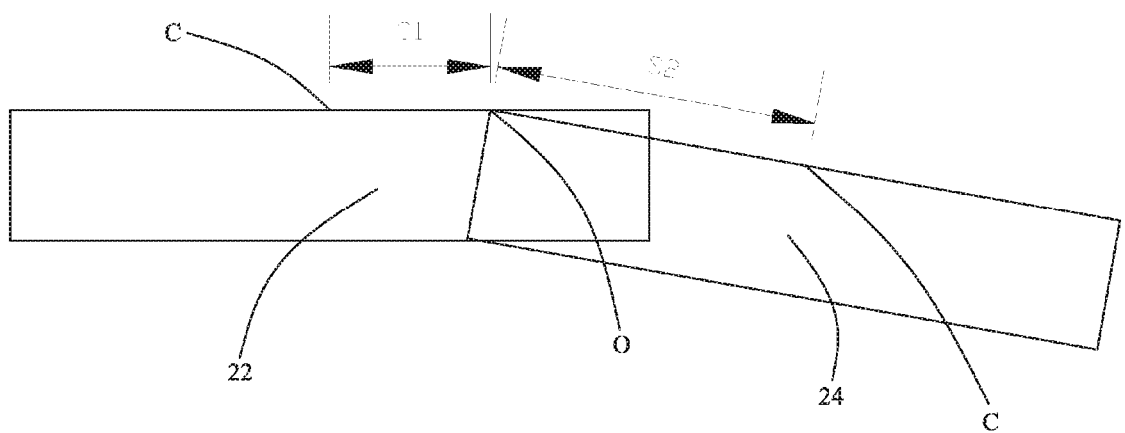

Further, as the positioning slot 246 of the second movable element 24 is in the arc shape, it has a corresponding center, i.e., a rotation center O of the second movable element 24. Term "rotation center" used herein indicates that a distance from any point of an element to the rotation center is constant when the element rotates around the rotation center. A bending direction of a moving trajectory of the second movable element 24 around the rotation center O thereof is opposite to the bending direction of the top surface 244 of the second movable element 24. In embodiments of the present disclosure, the rotation center O of the second movable element 24 is higher than a thickness center of the second movable element 24. In an embodiment of the present disclosure, the rotation center O of the second movable element 24 is flush with the top part of the supporting surface of the second movable element 24 or higher than the second movable element 24. As the rotation center O of the second movable element 24 is higher than the thickness center of the second movable element 24, a length difference caused by the thickness of the second movable element 24 in the rotation of the second movable element 24 around the rotation center O can be reduced. In order to make the expression clear and simple, as shown in FIGS. 13-15, it is assumed that, both the first movable element 22 and the second movable element 24 have cubic bodies, and centers C of top surfaces of the cubic bodies are the fixing points of the first movable element 22 and the second movable element 24, respectively, a distance between the center C of the top surface of the first movable element 22 and an end of the second movable element 24 adjacent to the first movable element 22 (hereinafter referred to as a first end of the second movable element 24) is recorded as S1, and a distance between the first end of the second movable element 24 and the center C of the top surface of the second movable element 24 is recorded as S2. If the rotation center O of the second movable element 24 is flush with the thickness center of the second movable element 24, as shown in FIG. 13, the distance between the center C of the top surface of the first movable element 22 and the center C of the top surface of the second movable element 24 is S1+S2 when the second movable element 24 does not rotate. As shown in FIG. 14, when the second movable element 24 rotates around the rotation center O, as the rotation center O is lower than the top surface of the second movable element 24, a displacement L is caused by the rotation of the first end of the second movable element 24 to its position before the rotation at the top surface of the first movable element 22. In such a case, along the top surfaces of the first movable element 22 and the second movable element 24, the distance between the center C of the top surfaces of the first movable element 22 and the center C of the second movable element 24 is S1+S2+L. Clearly, due to the displacement L, the length difference occurs at the distance between the center C of the top surface of the first movable element 22 and the center C of the top surface of the second movable element 24 along the top surfaces of the first movable element 22 and the second movable element 24. As shown in FIG. 15, if the rotation center O of the second movable element 24 is flush with the top surface of the second movable element 24, the distance between the center C of the top surface of the first movable element 22 and the center C of the top surface of the second movable element 24 along the top surfaces of the first movable element 22 and the second movable element 24 will always be S1+S2 when the second movable element 24 rotates around the rotation center O, thereby avoiding the length difference. Therefore, it can be seen that, in a thickness direction of the second movable element 24, from the thickness center to the top surface of the second movable element 24, the higher the rotation center O of the second movable element 24 is, the lower the length difference is.

On the contrary, the longer the length difference is, which indicates that the longer the distance from the center C of the top surface of the first movable element 22 to the center C of the top surface of the second movable element 24 along the top surfaces of the first movable element 22 and the second movable element 24 is. As the supporting plate 34 is fixed to the fixing point (i.e., the center C of the top surface) of the first movable element 22 and the fixing point (i.e., the center C of the top surface) of the second movable element 24 simultaneously, if the distance from the fixing point of the first movable element 22 to the fixing point of the second movable element 24 along the tops surfaces of the first movable element 22 and the second movable element 24 becomes longer, it means that the supporting plate 34 between the two fixing points will become longer correspondingly, thereby resulting in a tensile deformation of the supporting plate 34 between the two fixing points.

Based on principles described above, in order to reduce or prevent the tensile deformation of the supporting plate 34 between the two fixing points, in embodiments of the present disclosure, the rotation center O of the second movable element 24 is set to be higher than the thickness center of the second movable element 24, and more particularly to be flush with the fixing point of the second movable element 24. Certainly, the rotation center O may also be set at the supporting plate 34, and more particularly at a top surface (i.e., a first surface) of the supporting plate 34.

Further, in embodiments of the present disclosure, the top surfaces 224, 244 of the first movable element 22 and the second movable element 24 are arc surfaces, and together constitute a continuous arc surface when the second movable element 24 rotates around the first movable element 22, such that the flexible device as a whole is formed into a circular ring. Moreover, projections of the top surfaces 224, 244 of the first movable element 22 and the second movable element 24 in a plane perpendicular to the top surfaces 224, 244 together constitute a continuous arc. Therefore, part of the supporting plate 34 between the fixing point of the first movable element 22 and the fixing point of the second movable element 24 has to be bent into an arc consistent with the top surfaces 224, 244 of the first movable element 22 and the second movable element 24, so as to ensure that the supporting plate 34 can be tightly attached to the continuous arc surface constituted by the first movable element 22 and the second movable element 24 after the movement of the second movable element 24 relative to the first movable element 22. As a length of an arc is longer than that of a straight line, more particularly, a length of an arc defined together by the fixing point of the first movable element 22, the fixing point of the second movable element 24 and the rotation center O of the second movable element (it is set that the rotation center O is located at the top surface 224 of the first movable element 22) is greater than a sum of a linear distance from the fixing point of the first movable element 22 to the rotation center O of the second movable element 24 and a linear distance from the fixing point of the second movable element 24 to the rotation center O of the second movable element 24, if no correction is made, a length difference between the length of the arc and the linear distance will also result in the stretch of the supporting plate 34. Therefore, the rotation center O of the second movable element 24 should be further adjusted to reduce or offset the length difference between the length of the arc and the linear distance. Referring to FIGS. 11-12, in embodiments of the present disclosure, the rotation center O of the second movable element 24 should be higher than the top surface of the supporting plate 34, such that the second movable element 24 can further translate towards the first movable element 22 when rotating around the rotation center O, so as to reduce or offset the length difference between the length of the arc and the linear distance. In embodiments of the present disclosure, a ratio of a distance between the rotation center O of the second movable element 24 and the top surface of the supporting plate 34 to a thickness of the supporting plate 34 is between 0.1 and 0.5. As the rotation center O of the second movable element 24 is higher than the top surface of the supporting plate 34, a position of the rotation center O is constant relative to the first movable element 22, in other words, the position of the rotation center O relative to the first movable element 22 is unchanged with the movement of the second movable element 24 relative to the first movable element 22. Certainly, if the rotation center O is located at the top surface of the supporting plate 34 or the top surface 224 of the first movable element 22, the position of the rotation center O relative to the first movable element 22 is also constant. Further, the rotation center O may be located at the flexible functional screen 32 or even higher than the flexible functional screen 32. In addition, as the rotation center O of the second movable element 24 is higher than the top surface of the supporting plate 34, the rotation center O is higher than a lower part (i.e., the supporting plate 34) of the flexible functional element 30 with a higher hardness and higher than or flush with an upper part (i.e., the flexible functional screen 32) of the flexible functional element 30 with a lower hardness.

When the flexible device is in a first stat, such as in a plate state, the second movable element 24 is extended relative to the first movable element 22, the second movable element 24 is parallel to and flush with the first movable element 22, the first positioning shaft 260 of the first positioning element 26 is abutted against a first end of the positioning slot 246 of the second movable element 24. The second positioning shaft 262 of the first positioning element 26 is separated from a second end of the positioning slot 246 of the second movable element 24, and the first end and the second end are located at two opposite ends of the positioning slot 246, respectively. When the flexible device is in a second state (such as in a circular ring state), the second movable element 24 is retracted and inclined relative to the first movable element 22, an angle is formed between the first movable element 22 and the second movable element 24. The first positioning shaft 260 of the first positioning element 26 is separated from the first end of the positioning slot 246 of the second movable element 24, and the second positioning shaft 262 of the first positioning element 26 is abutted against the second end of the positioning slot 246 of the second movable element 24. Similarly, the second positioning element 28 has a position relationship similar to that of the first positioning element 26 when the flexible device is in different states, which will not be elaborated herein.

As the supporting plate 34 is only fixed to the top parts of the top surfaces 224, 244 of the first movable element 22 and the second movable element 24, a bottom surface (i.e., a second surface) of the supporting plate 34 is separated from other parts of the top surfaces 224, 244 of the first movable element 22 and the second movable element 24 when the flexible device is in the first state. The supporting plate 34 is in contact with other parts of the top surfaces 224, 244 of the first movable element 22 and the second movable element 24 when the flexible device is in the second state. When the flexible device is in the second state, the contact area between the supporting plate 34 and the top surface 224 of the first movable element 22 or the top surface 244 of the second movable element 24 is greater than that when the flexible device is in the first state.

In particular, a position on the top surface of the supporting plate 34 corresponding to the fixing point of the first movable element 22 is defined as a first reference point P1, and a position on the top surface of the supporting plate 34 corresponding to the fixing point of the second movable element 24 is defined as a second reference point P2. A length of an arc from the first reference point P1 to the second reference point P2 on the top surface of the supporting plate 34 when the flexible device is in the second state is equal to a linear distance between the first reference point P1 and the second reference point P2 when the flexible device is in the first state, Thereby, it is ensured that the length of the top surface of the supporting plate 34 is unchanged with the deformation of the flexible device.

It will be appreciated that, the first positioning element 26 may only include the first positioning shaft 260, then the first positioning element 26 is the first positioning shaft 260, and the positioning slot 246 of the second movable element 24 is shortened accordingly; also, the second positioning element 28 may only include the first positioning shaft 280, then the second positioning element 28 is the first positioning shaft 280, and the positioning slot 226 of the first movable element 22 is shortened accordingly, in such a configuration, the same effects as achieved in the configuration described hereinbefore where the first positioning shafts 260, 280 and the second positioning shaft 262, 282 are included simultaneously can also be achieved. It also will be appreciated that, in a certain case, the positioning element 202 may only include the second positioning element 28, then the positioning element 202 is the second positioning element 28. Correspondingly, the first movable elements 22 and the second movable elements 24 are stacked, for example, a $1^{st}$ first movable element 22 is disposed at an outer side of a $1^{st}$ second movable element 24, a $2^{nd}$ second movable element 24 is further disposed at an outer side of the $1^{st}$ first movable element 22, a $2^{nd}$ first movable element 22 is further disposed at an outer side of the $2^{nd}$ second movable element 24, and so on. Each positioning element 202 passes through an overlapped place of the corresponding first movable element 22 and second movable element 24. In such a case, the flexible device can also be transformed among different configurations, and stretch of the flexible functional element 30 will not occur or will be reduced. It will also be appreciated that, in extreme case, the flexible assembly 20 may only include one first movable element 22 and one second movable element 24 at each of the two opposite sides thereof; or only include one first movable element 22 at one of the two opposite sides thereof and one second movable element 24 at the other of the two opposite sides thereof; the flexible assembly 20 even may be disposed at the middle part of the casing 10, in these cases, the flexible device can also be switched among different configurations, and stretch of the flexible functional element 30 will not occur or will be reduced.

Further referring to FIG. 7, the casing 10 includes a plurality of connectors 100. These connectors 100 include several first connectors 12 and several second connectors 14. The first connectors 12 and second connectors 14 are alternately arranged and spaced apart from each other. The first connector 12 and the second connector 14 may be made of hard materials, such as plastics, metals and the like, so as to protect an electronic device contained in the casing 10. The first connector 12 and the second connector 14 may have the same or different structures. In embodiments of the present disclosure, the first connector 12 and the second connector 14 have different structures. The first connector 12 includes a baseplate 120 and side walls 122 extending upwards from two opposite ends of the baseplate 120, and the second connector 14 includes a baseplate 140 and side walls 142 extending upward from two opposite ends of the baseplate 140. The baseplate 120 of the first connector 12 includes two protruded steps 124, which are near the two opposite ends of the baseplate 120, respectively, and adjacent to the corresponding side wall 122; and the baseplate 140 of the second connector 14 includes two protruded steps 144 which are near the two opposite ends of the baseplate 140, respectively, and adjacent to the corresponding side wall 142. The first connector 12 includes a protruded baffle 126 on each step 124, and a height of the baffle 126 is greater than that of the step 124; the second connector 14 includes a protruded baffle 146 on each step 144, and a height of the baffle 146 is greater than that of the step 144. The baffle 146 of the second connector 14 is located at an inner side of the step 144 and away from the corresponding side wall 142, and the baffle 126 of the first connector 12 is located at an outer side of the step 124 and close to the corresponding side wall 122. The baffle 126 of the first connector 12 is spaced apart from the nearest side wall 122; and the baffle 146 of the second connector 14 is spaced apart from the nearest side wall 124. The first connector 12 and the second connector 14 remains spaced apart from each other and a slot is formed therebetween, no matter the flexible device is in the first state, the second state or other states between the first state and the second state. When the flexible assembly 20 is deformed, the first connector 12 and the second connector 14 moves relative to each other, but always remain spaced apart from each other.

The first connector 12 is provided with a screw hole in each step 124, and the second connector 14 is provided with a screw hole in each step 144. Each first connector 12 and one second connector 14 adjacent to the first connector 12 constitute a connector group to connect and support a movable element group constituted by one first movable element 22 and one second movable element 24 adjacent to the first movable element 22. The first connectors 12 and the second connectors 14 are arranged side by side, and the first movable element 22 and the second movable element 24 each are disposed on and abutted against top surfaces of the steps 124, 144 at the same side of the first connector 12 and the second connector 14. The first movable element 22 is close to the baffle 126 of the first connector 12, and the second movable element 24 is close to the baffle 146 of the second connector 14, such that the first movable element 22 and the second movable element 24 are misaligned from each other. The baffle 126 of the first connector 12 is abutted against the outer surface of the first movable element 22, and the baffle 146 of the second connector 14 is abutted against the inner surface of the second movable element 24, so as to together restrict the first movable element 22 and the second movable element 24 between the baffle 126 of the first connector 12 and the baffle 146 of the second connector 14. Two screws pass through the screw holes of the first connector 12 and the second connector 14 and enter into the bottom surfaces of the first movable element 22 and the second movable element 24, respectively, so as to further lock the first movable element 22 and the second movable element 24 on the first connector 12 and the second connector 14. A plurality of connector groups are successively connected in series to form the casing 10 of the flexible device, and a plurality of movable element groups are successively connected in series to form the flexible assembly 20 of the flexible assembly 20.

The first connector 12 is provided with a flange 128 on top part of each side wall 122 and close to an outer side of the side wall 122, and the flange 128 is higher than the top part of the side wall 122; the second connector 14 is provided with a flange 148 on top part of each side wall 142 and close to an outer side of the side wall 142, and the flange 148 is higher than the top part of the side wall 142. The top part of the side wall 122 is cooperated with the flange 128, and the top part of the side wall 142 is cooperated with the flange 148, so as to support and restrict the supporting plate 34. A bottom surface of a margin of the supporting plate 34 is abutted against the top surfaces of the side walls 122, 124, and a side surface of the margin of the supporting plate 34 is abutted against inner sides of the flanges 128, 148. Thereby, the margin of the supporting plate 34 at two opposite sides thereof is restricted by the flanges 128, 148.

Further referring to FIG. 3, the supporting plate 34 and the casing 10 together define a hollow chamber for accommodating the electronic device. The electronic device may include a controller 40 for controlling the functional element 30, a battery 50 (i.e., a first battery) for supplying power to the functional element 30 and the controller 40, and a communication module for communicating the flexible device with an outside electronic equipment.

Furthermore, the functional element 30 is not limited to the flexible touch screen or the flexible display mentioned above, and may also include other types of functional elements, such as other types of display screens/indicators, functional sensors, speakers, microphones and so on, according to different requirements. Other types of display screens/indicators may be such as hard displays, electronic ink screens, LED luminescent plates in various sizes, which can be fixed on the top surface of the supporting plate 34. The functional sensors may include a body temperature sensor, a temperature sensor, a speed sensor, a gravity sensor, a height sensor, an angular velocity sensor, an acceleration sensor, a pressure sensor, a heart rate sensor, a pulse sensor, a sweat sensor, a light sensor, an electromyography sensor and so on, which may be disposed at different positions of the flexible device, such as the top surface of the supporting plate 34, the chamber defined by the supporting plate 34 and the casing 10, or the bottom surface of the casing 10, etc., according to different use purpose. The speaker and microphone may also be disposed in the chamber defined by the supporting plate 34 and the casing 10.

Figure 16:
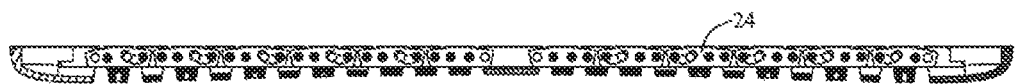
FIG. 16 is a sectional view of the flexible device as shown in FIG. 1.
Figure 17:
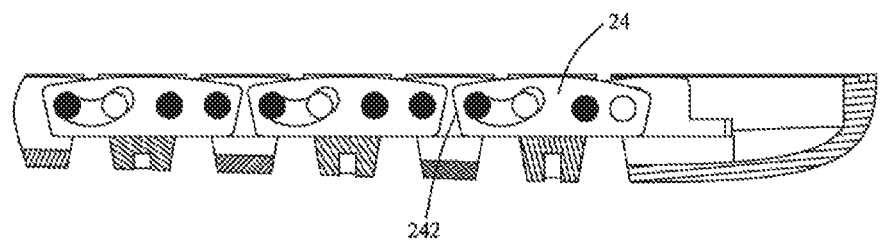
FIG. 17 is a partially enlarged view of the flexible device as shown in FIG. 16.
Figure 18:
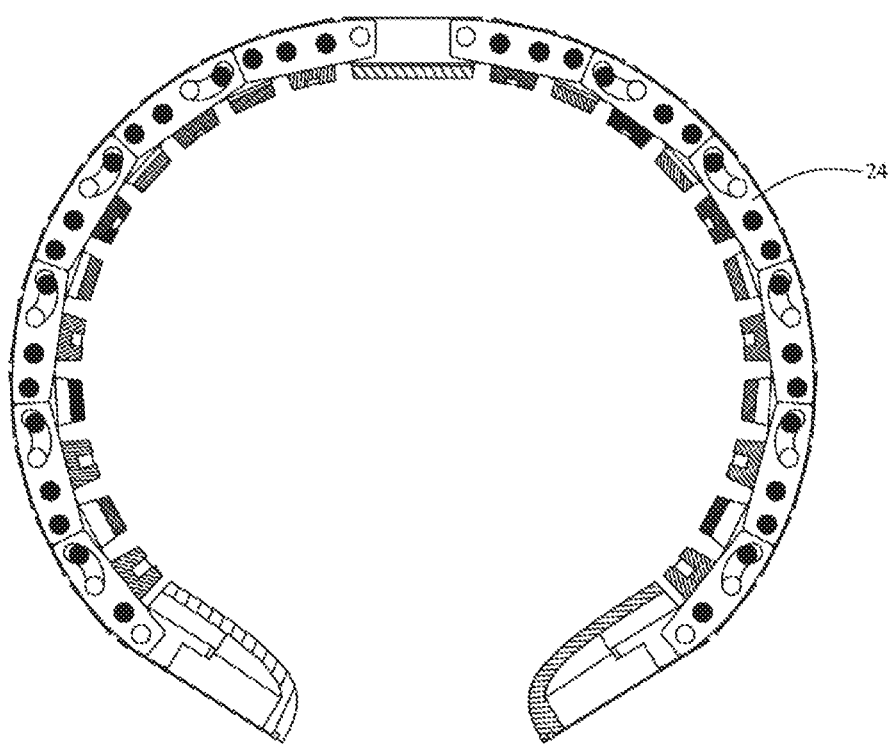
FIG. 18 is a sectional view of the flexible device as shown in FIG. 4.

Further referring to FIGS. 16-18, when the flexible device is needed to be switched to the first state, the flexible device can be spread out, in such a case, the supporting plate 34 is in the plate shape, the first movable elements 22 at each side of the flexible device are arranged in a line, and the second movable elements 24 at each side of the flexible device are also arranged in a line. Adjacent first movable elements 22 are spaced apart from each other with the side surfaces 222 of adjacent first movable elements 22 forming a gap, and the gap between the adjacent first movable elements 22 gradually increases in width from top to bottom, thereby forming a trapezoidal shape. Adjacent second movable elements 24 are spaced apart from each other with the side surfaces 222 of adjacent first movable elements 22 forming a gap, and the gap between the adjacent second movable elements 24 gradually increases in width from top to bottom, thereby forming a trapezoidal shape. The top surface of the first movable element 22 and the top surface of the second movable element 24 adjacent to the first movable element 22 are not distributed continuously. When the flexible device is needed to be switched to the second state, the flexible device is bent, in such a case, the supporting plate 34 is in an arc shape with a radian less than 360 degrees. The first movable elements 22 at each side of the flexible device are arranged into an arc shape, and the second movable elements 24 at each side of the flexible device are arranged into an arc shape. Adjacent first movable elements 22 are abutted against each other, and a side surface 222 of one of the adjacent first movable elements 22 is in contact with a side surface 222, opposite to the side surface 222 of one of the adjacent first movable elements 22, of the other of the adjacent first movable elements 22. Adjacent second movable elements 24 are abutted against each other, and a side surface 242 of one of the adjacent second movable elements 24 is in contact with a side surface 242, opposite to the side surface 242 of one of the adjacent second movable elements 24, of the other of the adjacent second movable elements 24. As a consequence, a bending degree of the flexible device is restricted within a required range. In particular, after bending, the top surfaces of the first movable elements 22 at each side of the flexible device together constitute a continuous arc with a radian greater than 270 degrees, and the top surfaces of the second movable elements 22 at each side of the flexible device also together constitute a continuous arc with a radian greater than 270 degrees. As a consequence, the flexible touch screen or the flexible display can be presented as a near-perfect ring, thereby giving a better experience to the user no matter in using or in viewing. In the second state, the flexible device can be worn on the wrist of the user to act as a smart bracelet. Of course, in the second state, the flexible device can also be worn on the arm, waist, thigh, calf, neck, forehead, etc.

Due to the use of the first movable element 22 and the second movable element 24, the flexible assembly 20 in embodiments of the present disclosure not only has a higher strength and a longer longevity as compared with the material having flexibility per se (such as soft plastic, fabric band, etc.), but can be formulated to have a required bending angle, thereby having a wider application range and meeting the application requirements at different occasions. Of course, the flexible assembly 20 may also be made of flexible materials in some situations where requirements are not high.

In addition, considering that the electronic devices, such as the controller 40, the battery 50, the communication module, etc., are not resistant to bending, in order to protect these electronic devices, the casing 10 may further include two end covers 16 disposed at two opposite ends of the flexible device, respectively. The two end covers 16 have the same structure and are arranged symmetrically. Each end cover 16 may be manufactured with the same hard material as the first connector 12 and the second connector 14. Each end cover 16 includes a baseplate 160 and a side wall 162 extending upward from a margin of the baseplate 160. The baseplate 160 is substantially in a semicircular shape, and its area is larger than an area of the baseplate 120 of the first connector 12 or the baseplate 140 of the second connector 14, and larger than a total area of the baseplates 120, 140 of the first connector 12 and the second connector 14. The baseplate 160 is provided with two steps 164 at two opposite sides and close to the margin thereof, and each step 164 is provided with two screw holes at a top surface thereof. The side wall 162 is provided with a flange on a top surface and close to an outer side thereof. The supporting plate 34 is also abutted against the top surface of the side wall 162 and an inner side of the flange. Due to the larger area of the baseplate 160, the end cover 16 can provide a larger space to accommodate the electronic devices which are not resistant to bending. For example, the battery 50 can be accommodated in one end cover 16, and the electronic devices like the controller 40, the communication module and a circuit board can be accommodated in the other end cover 16. The battery 50 is connected with the controller 40, the communication module and the circuit board through a wire. The flexible touch screen or flexible display is connected with the circuit board through a flexible circuit board, thereby realizing the electrical connection with the controller 40, the communication module and the battery 50. As the battery 50 and the controller 40 are respectively disposed in the two end covers 16, they also respectively located at two opposite ends of the flexible assembly 20. The battery 50 and the controller 40 will move along with the deformation of the flexible assembly 20, and a distance between the battery 50 and the controller 40 will be changed also. In particular, the distance between the battery 50 and the controller 40 will decrease with deformation of the flexible assembly 20 towards the second state.

By setting the battery 50 and other electronic devices in two separated end covers 16, inner space of the flexible device can be effectively saved, thereby enabling the flexible device to be lighter, thinner and smaller. Furthermore, the separation of the battery 50 from other electronic devices can also prevent an interaction between the battery 50 and other electronic devices caused by heat generated during their operations, thereby ensuring normal operations of the battery 50 and other electronic devices.

Figure 10:
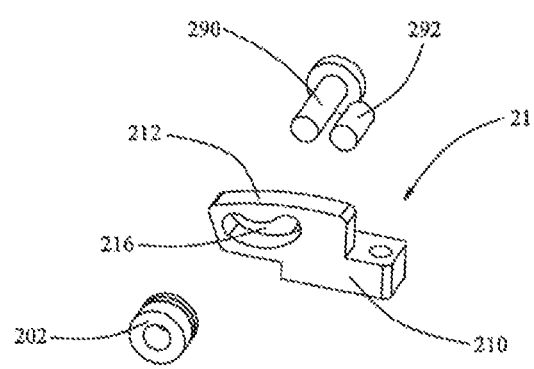
FIG. 10 is another partial enlarged view of the flexible device as shown in FIG. 8.

Referring to FIG. 10, the flexible assembly 20 may further include a third movable element 21 for connecting the end cover 16 with the first movable element 22 or the second movable element 24 adjacent to the end cover 16. The third movable element 21 includes a pedestal 210 and a plate 212 disposed on a top surface of the pedestal 210. The pedestal 210 is parallel to the top surface of the step 164 of the end cover 16, and the plate 212 is perpendicular to the top surface of the step 164. The plate 212 has a shape similar to that of a part having the positioning slot 226, 246 of the first movable element 22 or the second movable element 24, and is also provided with a positioning slot 216. The positioning slot 216 of the plate 212 has the same shape as that of the positioning slot 226, 246 of the first movable element 22 or the second movable element 24. Similar to the first movable element 22 or the second movable element 24, a positioning element 202 passes through the positioning slot 216 of the plate 212 and enters into the positioning hole 228, 248 of the first movable element 22 or the second movable element 24 adjacent to the third movable element 21, so as to movably connect the third movable element 21 with the first movable element 22 or the second movable element 24 adjacent to the third movable element 21. The positioning element 202 includes a first positioning shaft 290 and a second positioning shaft 292, and an end of the first positioning shaft 290 is locked in a restricting element 204 after passing through the first movable element 22 or the second movable element 24 adjacent to the third movable element 21. The restricting element 204 has a same structure and function as that of the restricting element 204 described hereinbefore. The pedestal 210 is locked on the top surface of the step 164 of the end cover 16 through a fastener, such as a screw.

Figure 8:
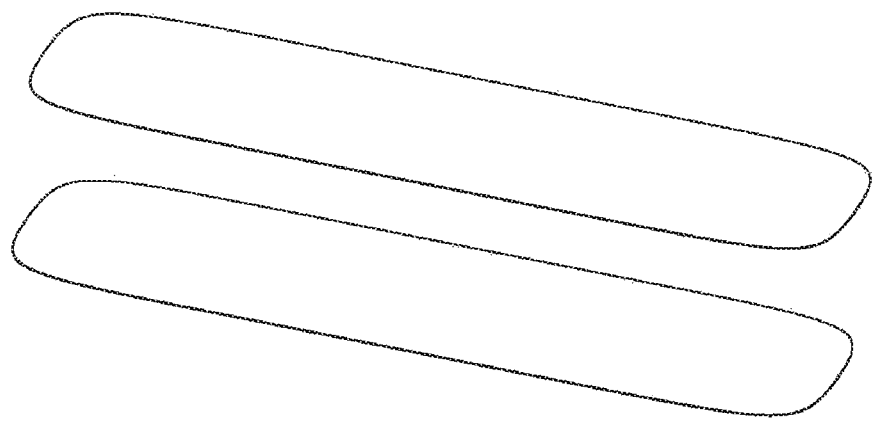
FIG. 8 is a partial explosive view of the flexible device as shown in FIG. 1.
Figure 8:
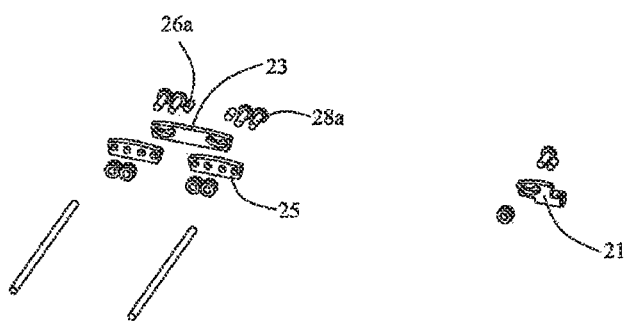
Figure 8:
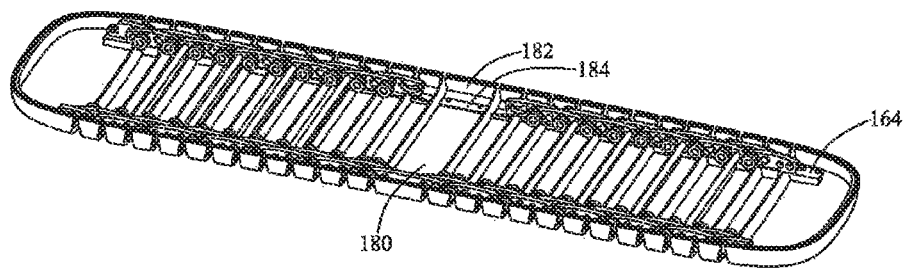
Figure 9:
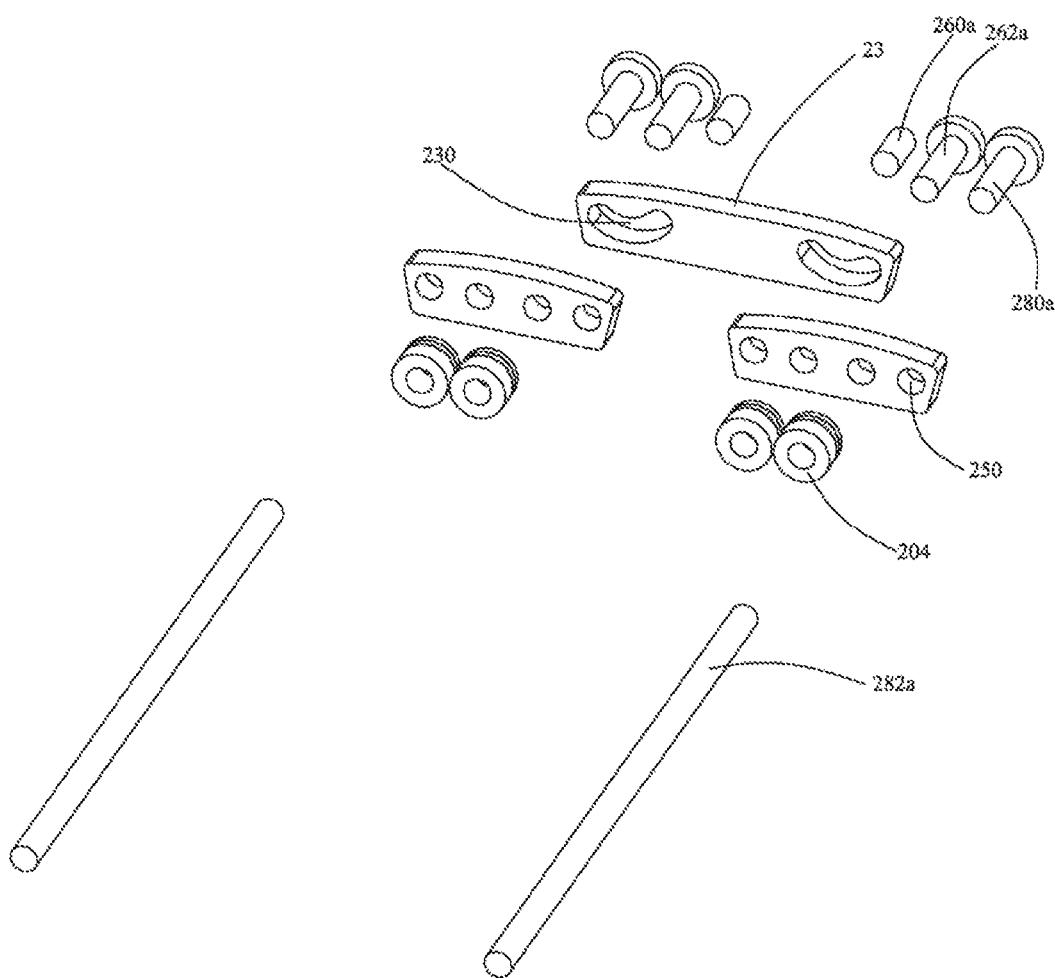
FIG. 9 is a partial enlarged view of the flexible device as shown in FIG. 8.

Further referring to FIGS. 8-9, due to the limited space of the end cover 16, a capacity of the battery 50 accommodated in the end cover 16 is limited. In order to enable the flexible device to be used for a longer time, the flexible device may be provided with another battery 60 (i.e., a second battery 60). Capacity of the battery 60 is less than that of the battery 50. The battery 60 may be disposed at a suitable position of the flexible device according to requirements. In embodiments of the present disclosure, the battery 60 is disposed at the middle part of the flexible device. Correspondingly, a protecting structure is provided at the middle part of the flexible device to prevent the battery 60 from being bent. Specifically, the casing 10 of the flexible device is provided with a third connector 18 at the middle part thereof. The third connector 18 has a structure similar to that of the first connector 12 or the second connector 14, except that the third connector 18 has a larger area as compared with that of the first connector 12 or the second connector 14. The third connector 18 includes a baseplate 180, a side wall 182 and a step 184, which have structures similar to that of the corresponding parts of the first connector 12 or the second connector 14, except for the larger size in width. In embodiments of the present disclosure, the baseplate 180 of the third connector 18 has a width more than two times of that of the baseplate 120 of the first connector 12 or the baseplate 140 of the second connector 14, so as to accommodate the battery 60. Correspondingly, the flexible assembly 20 further includes a fourth movable element 23 and a fifth movable element 25. The fourth movable element 23 is composed of two symmetrical plates (i.e., a left plate and a right plate), and each plate has a structure and shape similar to that of the part including the positioning slot 226, 246 of the first movable element 22 or the second movable element 24. Top surfaces of the two plates together constitute a continuous arc surface to serve as a supporting surface, and a top part of the supporting surface is served as a fixing point fixed to the bottom surface of the supporting plate 34. Each plate is provided with a positioning slot 230, which has a shape and structure similar to that of the positioning slot 226 of the first movable element 22 or the positioning slot 246 of the second movable element 24. In particular, the positioning slot 230 of the left plate is slightly tilted to a left side of the fourth movable element 23, and the positioning slot 230 of the right plate is slightly tilted to a right side of the fourth movable element 23. Two fifth movable elements 25 are movably connected to two opposite sides of the fourth movable element 23, respectively. Shape and structure of the fifth movable element 25 are basically the same as that of the first movable element 22 or the second movable element 24, except that the fifth movable element 25 is provided with two through-holes at a position corresponding to the positioning slot 226, 246 of the first movable element 22 or the second movable element 24. Therefore, the fifth movable element 25 has four through-holes 250, two of which are close to the fourth movable element 23 and referred as first through-holes 250, and the other two of which are far away from the fourth movable element 23 and referred as second through-holes 250. The two first through-holes 250 are movably connected with the fourth movable element 23 through a positioning element 202, and the two second through-holes 250 are movably connected with the first movable element 22 or the second movable element 24 adjacent to the fifth movable element 25 through a positioning element 202. In embodiments of the present disclosure, the positioning element 202 connecting the fifth movable element 25 and the fourth movable element 23 includes a first positioning element 26*a*, which includes a first positioning shaft 260*a* and a second positioning shaft 262*a*. The first positioning shaft 260*a* includes a pillar, and the second positioning shaft 262*a* includes a screw. The pillar has a same shape and structure as that of the pillar mentioned hereinbefore, and the screw has a same shape and structure as that of the screw mentioned hereinbefore. The pillar and screw pass through the positioning slot 230 of the fourth movable element 23 and enter into two through-holes 250 of the fifth movable element 25, respectively. Moreover, an end of the screw is locked in the restricting element 204 after passing through the fifth movable element 25. The positioning element 202 connecting the fifth movable element 25 and the first movable element 22 or second movable element 24 adjacent to the fifth movable element 25 includes a second positioning element 28a, which includes a first positioning shaft 280a and a second positioning shaft 282a. The first positioning shaft 280a includes a screw, and a second positioning shaft 282a includes a connecting rod. The screw has a same shape and construction as that of the screw mentioned hereinbefore, and the connecting rod has a same shape and construction as that of the connecting rod mentioned hereinbefore. The screw and connecting rod pass through the positioning slot 226, 246 of the first movable element 22 or the second movable element 24 and enter into two through-holes 250 of the fifth movable element 25, respectively. Moreover, an end of the screw is locked in the restricting element 204 after passing through the fifth movable element 25. An end of the connecting rod passes through a fifth movable element 25 at one of the two opposite sides of the flexible device and enters into a fifth movable element 25 and a first movable element 22 or a second movable element 24 at the other of the two opposite sides of the flexible device, so as to fasten the flexible device. Particularly, the connecting rod is disposed in the through-hole of the fifth movable element 25 which is farthest from the fourth movable element 23, thereby leaving a sufficient space between two connecting rods to accommodate the battery 60 and avoiding such a case that a distance between the two connecting rods is too short to displace the battery 60.

With the cooperation of the two batteries 50, 60, the using time of the flexible device can be effectively increased. Moreover, since the battery 60 is disposed in the middle part of the flexible device, when the flexible device is used as a smart bracelet, the battery 60 is located at a position corresponding to a backside, a flattest part, of the wrist, so that the bottom of the baseplate 180 of the third connector 18 can be effectively attached to the backside of the wrist, thereby reducing or eliminating discomfort caused by the inconsistent flatness of attached faces.

What is claimed is:
1. A flexible device, comprising:
a functional element;
a first movable element;
a second movable element movably connected with the first movable element,
wherein a movement of the second movable element relative to the first moveable element drives the flexible device to deform and the movement of the second movable element relative to the first movable element is switched between a first state and a second state, in the first state, the second movable element extends relative to the first movable element, and in the second state, the second movable element retracts relative to the first movable element;
wherein the second movable element defines a rotation center, and the rotation of the second movable element around the rotation center drives the flexible device to deform;
wherein top surfaces of the first movable element and the second movable element each comprises a convex surface, the convex surfaces of the first movable element and the second movable element are each an arc surface;

wherein the second state, projections of the convex surfaces of the first movable element and the second movable element in a plane perpendicular to the convex surfaces together form a continuous arc.

2. The flexible device according to claim 1, wherein the movement of the second movable element relative to the first movable element comprises translation and rotation.

3. The flexible device according to claim 1, wherein the rotation center of the second movable element is higher than a top part of the second movable element.

4. The flexible device according to claim 1, wherein hardness of a lower part of the functional element is greater than that of an upper part of the functional element, and the rotation center of the second movable element is higher than the lower part of the functional element.

5. The flexible device according to claim 1, wherein in the second state, the convex surfaces of the first movable element and the second movable element together constitute a continuous arc surface.

6. The flexible device according to claim 1, wherein in the first state, the convex surfaces of the first movable element and the second movable element are not distributed continuously.

7. The flexible device according to claim 1, wherein the functional element comprises a supporting plate and a flexible functional screen attached to the supporting plate; the supporting plate comprises a first surface fixed to the flexible functional screen, and a second surface fixed to the first movable element and the second movable element; and the first surface and the second surface are disposed on two opposite sides of the supporting plate, respectively.

8. The flexible device according to claim 7, wherein the rotation center of the second movable element is higher than the first surface of the supporting plate.

9. The flexible device according to claim 7, wherein the second surface of the supporting plate is fixed to top parts of the top surfaces of the first movable element and the second movable element; in the first state, the second surface of the supporting plate separates from other parts of the top surfaces of the first movable element and the second movable element; and in the second state, the second surface of the supporting plate contacts with other parts of the top surfaces of the first movable element and the second movable element;
a contact area between the supporting plate and the top surface of the second movable element in the second state is greater than that in the first state.

10. The flexible device according to claim 7, wherein a hardness of the supporting plate is greater than that of the flexible functional screen.

11. The flexible device according to claim 7, wherein a ratio of a distance between the rotation center of the second movable element and the first surface of the supporting plate to a thickness of the supporting plate is between 0.1 and 0.5.

12. The flexible device according to claim 1, wherein a location of the rotation center of the second movable element relative to the first movable element is constant when the second movable element moves relative to the first movable element.

13. The flexible device according to claim 1, wherein the second movable element is staggeredly connected with the first movable element.

14. The flexible device according to claim 1, wherein a rotation trajectory of the second movable element around the rotation center is in an arc shape, and a bending direction of the arc trajectory of the second movable element is opposite to that of the top surface of the second movable element.

15. A flexible device, comprising:
a functional element;
a first movable element;
a second movable element movably connected with the first movable element,
wherein a movement of the second movable element relative to the first moveable element drives the flexible device to deform and the movement of the second movable element relative to the first movable element is switched between a first state and a second state, wherein in the first state, the second movable element extends relative to the first movable element, and in the second state, the second movable element retracts relative to the first movable element;
wherein the second movable element defines a rotation center, and the rotation of the second movable element around the rotation center drives the flexible device to deform;
wherein top surfaces of the first movable element and the second movable element each comprises a convex surface, the convex surfaces of the first movable element and the second movable element are each an arc surface;
wherein the second movable element provides an arc positioning slot, along which the second movable element is configured to move relative to the first movable element, two opposite ends of the positioning slot are near the top surface of the second movable element, and a middle part of the positioning slot is away from the top surface of the second movable element.

16. The flexible device according to claim 15, wherein a bending direction of the positioning slot is opposite to that of the top surface of the second movable element.

17. A flexible device, comprising:
a casing;
a functional element disposed on the casing;
a plurality of movable elements positioned at each of two opposite sides of the casing;
wherein the movable element comprises a first movable element and a second movable element movably connected with the first movable element;
a movement of the second movable element relative to the first moveable element drives the flexible device to deform and the movement of the second movable element relative to the first movable element is switched between a first state and a second state, in the first state, the second movable element extends relative to the first movable element, and in the second state, the second movable element retracts relative to the first movable element;
wherein top surfaces of the first movable element and the second movable element each comprises a convex surface, the convex surfaces of the first movable element and the second movable element are each an arc surface and
in the second state, projections of the convex surfaces of the first movable element and the second movable element in a plane perpendicular to the convex surfaces together form a continuous arc.

18. The flexible device according to claim 17, wherein the movement of the second movable element relative to the first movable element comprises translation and rotation.

19. The flexible device according to claim 17, wherein the second movable element defines a rotation center, and the rotation of the second movable element around the rotation center drives the flexible device to deform, the rotation center of the second movable element is higher than a top part of the second movable element.

* * * * *